United States Patent
Meyer (10) Patent No.: US 10,028,772 B2
(45) Date of Patent: Jul. 24, 2018

(54) OSTEOTOMY INSTRUMENT

(71) Applicant: Alphatec Spine, Inc., Carlsbad, CA (US)

(72) Inventor: Nathan Meyer, Vista, CA (US)

(73) Assignee: Alphatec Spine, Inc., Carlsbad, CA (US)

(*) Notice: Subject to any disclaimer, the term of this patent is extended or adjusted under 35 U.S.C. 154(b) by 407 days.

(21) Appl. No.: 14/877,587

(22) Filed: Oct. 7, 2015

(65) Prior Publication Data
US 2016/0095634 A1 Apr. 7, 2016

Related U.S. Application Data

(60) Provisional application No. 62/060,818, filed on Oct. 7, 2014.

(51) Int. Cl.
*A61B 17/70* (2006.01)

(52) U.S. Cl.
CPC ...... *A61B 17/7077* (2013.01); *A61B 17/7032* (2013.01)

(58) Field of Classification Search
CPC ............ A61B 17/7074; A61B 17/7079; A61B 17/7077; A61B 17/708; A61B 17/7083; A61B 17/60; A61B 17/64; A61B 17/6433; A61B 17/66; A61B 2017/0256
See application file for complete search history.

(56) References Cited

U.S. PATENT DOCUMENTS

| | | | | |
|---|---|---|---|---|
| 2,002,021 A * | 5/1935 | Rouse | ............... | A61B 17/6408 606/105 |
| 3,960,147 A * | 6/1976 | Murray | ............. | A61B 17/0642 411/474 |
| 5,899,901 A * | 5/1999 | Middleton | ........ | A61B 17/7032 606/102 |
| 6,017,342 A * | 1/2000 | Rinner | ............... | A61B 17/8866 606/57 |
| 6,716,218 B2 * | 4/2004 | Holmes | ............. | A61B 17/7079 606/105 |
| 8,951,258 B2 * | 2/2015 | Peultier | ............. | A61B 17/7077 606/279 |
| 9,402,660 B2 * | 8/2016 | Brinkman | ............ | A61B 17/708 |
| 9,622,795 B2 * | 4/2017 | Reitblat | ............ | A61B 17/7077 |
| 9,795,370 B2 * | 10/2017 | O'Connell | ........ | A61B 17/0206 |

(Continued)

*Primary Examiner* — Jacqueline Johanas
(74) *Attorney, Agent, or Firm* — Honigman Miller Schwartz and Cohn LLP (57) ABSTRACT

An osteotomy instrument includes a handle, a first arm assembly, a second arm assembly, a displacement mechanism, and a tuning mechanism. The first arm assembly is pivotably mounted to the handle. The first arm assembly includes a first fastener support configured to hold a fastener. The second arm assembly is pivotably mounted to the handle. The second arm assembly includes a second fastener support configured to hold a fastener. The displacing mechanism includes a dial disposed on the handle. The displacing mechanism is configured to laterally displace a distal end of the first arm assembly and second arm assembly away and towards each other. The dial actuates the displacing mechanism. The tuning mechanism is configured to change an angular position of the first fastener support with respect to the second fastener support.

19 Claims, 7 Drawing Sheets

(56) References Cited

U.S. PATENT DOCUMENTS

| | | | | |
|---|---|---|---|---|
| 2005/0245928 A1* | 11/2005 | Colleran | ............... | A61B 17/708 606/90 |
| 2007/0270874 A1* | 11/2007 | Anderson | ............ | A61B 17/025 606/90 |
| 2008/0077155 A1* | 3/2008 | Diederich | ............ | A61B 17/708 606/105 |
| 2008/0125788 A1* | 5/2008 | Cohen | ................. | A61B 17/7076 606/104 |
| 2009/0228051 A1* | 9/2009 | Kolb | ................. | A61B 17/7032 606/305 |
| 2012/0197297 A1* | 8/2012 | Bootwala | ........... | A61B 17/7077 606/246 |
| 2012/0239096 A1* | 9/2012 | Gleeson | ............... | A61B 17/708 606/86 A |
| 2012/0296171 A1* | 11/2012 | Lovell | ............... | A61B 17/0206 600/213 |
| 2012/0303034 A1* | 11/2012 | Woolley | ............. | A61B 17/0206 606/90 |
| 2014/0249591 A1* | 9/2014 | Peultier | .............. | A61B 17/7077 606/86 A |
| 2014/0277167 A1* | 9/2014 | Hutton | ............... | A61B 17/7032 606/279 |
| 2015/0066088 A1* | 3/2015 | Brinkman | .......... | A61B 17/7077 606/264 |

* cited by examiner

OSTEOTOMY INSTRUMENT

CROSS-REFERENCE TO RELATED APPLICATIONS

This application claims priority of U.S. Provisional Application 62/060,818 filed Oct. 7, 2014, the contents of which are incorporated herein by reference.

TECHNICAL FIELD

An osteotomy instrument having a pair of arm assemblies laterally displaced from each other by a displacing mechanism so as to facilitate positioning and maintaining spatial relationship between vertebrae by a single operator is provided.

BACKGROUND OF THE INVENTION

Osteotomy tools for assisting in osteotomy procedures are known. Specifically, osteotomy tools to assist with pedicle substraction osteotomy are known. Such tools commonly include a pair of arms laterally displaced from each other so as to set vertebrae in a desired position. Current instruments require the operator to use both hands to set the arms in a corresponding position. The instrument may then be applied to the vertebrae via pedicle screws inserted into the spine so as to stabilize spaced apart vertebrae during a surgical procedure.

It is known to couple a pair of pedicle screws on each of the pair of tool arms, so as to have an inner pedicle screw and an outer pedicle screw. Current osteotomy instruments have two mechanisms, and each mechanism mounted to a respective tool arm allows for limited positioning of an outer pedicle screw with respect to the inner pedicle screw.

Accordingly, it remains desirable to have an osteotomy instrument configured to be held and operated by a single user, and wherein the pedicle screws may be pivoted utilizing a single mechanism so as to reduce the procedure time and distribute applied forces more evenly to the vertebrae.

SUMMARY OF THE INVENTION

An osteotomy instrument configured to be operated by a single user is provided, wherein the instrument may be held by one hand and alignment and positioning of pedicle screws may be adjusted by the other hand. The instrument includes a handle, a first arm assembly and a second arm assembly. The first arm assembly is pivotably mounted to the handle. The first arm assembly includes a first fastener support configured to hold a fastener. The second arm assembly is pivotably mounted to the handle. The second arm assembly includes a second fastener support configured to hold a fastener.

The osteotomy instrument includes a displacing mechanism and a tuning mechanism. The displacement mechanism includes a dial disposed on the handle. The dial actuates the displacing mechanism. The displacing mechanism is configured to translate an axial movement of the proximal ends of the first and second arm assemblies into a lateral displacement of the distal ends of the first and second arm assemblies. Accordingly, the pedicle screws may be laterally displaced with respect to each other.

The tuning mechanism is configured to change an angular position of the first fastener support with respect to the second fastener support. The tuning mechanism is configured to adjust the angular position of the first fastener support of the first arm assembly with respect to the second fastener support of the second arm assembly. The tuning mechanism is configured to translate a rotary movement of a dial into an angular displacement of the fastener support so as to adjust the angular displacement or position of the outer pedicle screw with respect to the inner pedicle screw.

The instrument further includes a fastener housing configured to hold a receiver of a fastener. The fastener housing is mounted on the fastener support and may be slidably mounted to the fastener support, or in the alternative, be integral with the fastener support. The fastener housing includes an eject mechanism configured to release the fastener from the fastener housing. The eject mechanism may be actuated by a simple push, thus allowing the operator to disengage the instrument from the organic subject matter after the fasteners have been inserted.

In a preferred embodiment the displacing mechanism includes a dial having a threaded shaft. The dial may be disposed at a free end of the handle and the threaded shaft is disposed within the handle. The handle includes a slotted end configured to hold the proximal ends of the first and second arm assemblies. The threaded shaft is configured to engage a stud that is slidably received within a bore of the handle. The handle also includes a slot.

A stud pin extends between a distal end of the stud and is engaged with displacement mechanism wherein the displacement assembly is configured to expand and retract with the axial movement of the threaded shaft within the bore. The displacement mechanism includes a first leg and a second leg, and the proximal ends of each of the first and second legs are pivotably mounted to the stud pin. Thus, the proximal ends of the first and second legs are rotatably coupled to the stud and movable up and down the bore.

Specifically, rotation of the dial engages the bore so as to move the bore up and down along the threaded shaft wherein the first and second legs are attached to the distal end of the stud by the stud pin.

The distal ends of the first and second legs are mounted to a respective proximal end of an inner secondary arm of each of the first and second arm assemblies. Thus, as the stud travels up and down the threaded shaft, the distal ends of the first and second legs displace the proximal ends of the inner secondary arms of the first and second arm assemblies, which in turn moves the first and second legs towards each other as the bore traverses up the threaded shaft towards the handle and away from each other as the stud travels down the threaded shaft.

The tuning mechanism is configured to adjust the angular position of the first fastener support of the first arm assembly with respect to the second fastener support of the second arm assembly. The tuning mechanism includes a pair of U-shaped brackets. The U-shaped brackets are mounted within a carrier. A pair of wheel gears which can be rotated using a tuning dial is also held within the carrier. The pair of wheel gear is configured to engage teeth within an interior of the U-shaped bracket such that the wheel gear travels up and down along a slot defined by the U-shape. Movement of the pair of wheel gears within the slots displaces an end of an outer primary arm of each of the first arm assembly and the second arm assembly so as to pivot an outer edge of the fastener support relative to an inner edge of the fastener support.

Furthermore, inner fasteners are disposed on the inner edge of each of the first and second fastener supports, and outer fasteners are disposed on the outer edge of the first and second fastener supports. Accordingly, the user may simply hold the instrument by the handle and turn the dial so as to adjust the displacement of the distal ends of the first and second arm assembly with respect to each other, and turn the tuning dial so as to vary an angular position of the outer and inner fasteners of the first fastener support with respect to the outer and inner fasteners of the second fastener support.

Each of the first and second fastener supports are a generally elongated bar having a pair of fastener housings configured to hold a fastener. The fastener housings each include an ejector mechanism having a lever configured to disengage the fastener from the fastener housing.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be better understood when read in conjunction with the following drawings where like structure is indicated with like reference numerals and in which:

DETAILED DESCRIPTION OF THE PREFERRED EMBODIMENTS

The embodiments described herein generally relate to an osteotomy instrument configured to position, stabilize, and support the spine during surgical procedures. The instrument includes a handle configured to be gripped by one hand, and first and second arm assemblies configured such that each arm assembly includes a fastener support that holds a pair of fasteners such as pedicle screws. The instrument is further configured to be used by one person wherein one hand may grip the handle so as to steady the instrument for insertion and the other hand may actuate a displacing mechanism or a tuning mechanism so as to position the instrument and pedicle screws for a surgical procedure such as substraction.

The displacement mechanism is configured to laterally displace distal ends of a first arm assembly and a second arm assembly. The displacement mechanism may be actuated from a location at a proximal end of the handle. The displacement mechanism may include a rotary member, e.g. a dial, configured to translate a rotary movement into a lateral displacement of the distal ends of the first and second arm assemblies. Accordingly, the displacement mechanism adjusts the displacement of the fasteners laterally with respect to each other.

The tuning mechanism may be actuated by one hand as the other hand grips the handle. The tuning mechanism may include a tuning dial configured to translate a rotary movement into an angular displacement or position of the first fastener support of the first arm assembly with respect to the second fastener support of the second arm assembly. The tuning mechanism may be configured to simultaneously angle each of the first fastener housing and the second fastener housing to pivot the outer fasteners of the first and second fastener housing with respect to the inner fasteners of the first and second fastener housings. Thus, the instrument reduces operation time by expediting the adjustment of the fasteners with respect to each other.

The instrument may further include an ejecting mechanism. The ejecting mechanism may be configured to detach the fasteners from the respective first and second arm assemblies. The ejecting mechanism is configured to be actuated by one hand while the other hand grips the handle.

In operation, the user may grasp the handle and actuate the displacing mechanism so as to adjust the lateral displacement of the fasteners in the first fastener support with respect to fasteners in the second fastener support. The fasteners may then be inserted into the vertebrae so as to stabilize the vertebrae for surgical procedures. The tuning mechanism may also be actuated so as to angularly position the outer and inner fasteners of the first fastener support with respect to the outer and inner fasteners of the second fastener support. Specifically, angle of the outer and inner fasteners with respect to a longitudinal axis of the handle is adjusted and thereby place the vertebrae in a desired disposition.

Upon completion of the surgical procedure the fasteners may be detached from the instrument by actuation of an ejector mechanism. Accordingly, the instrument facilitates orthopedic procedures by allowing the user to grip the instrument while making adjustments to the fasteners, and then detaching the pedicle screws from the instrument.

Figure 1:
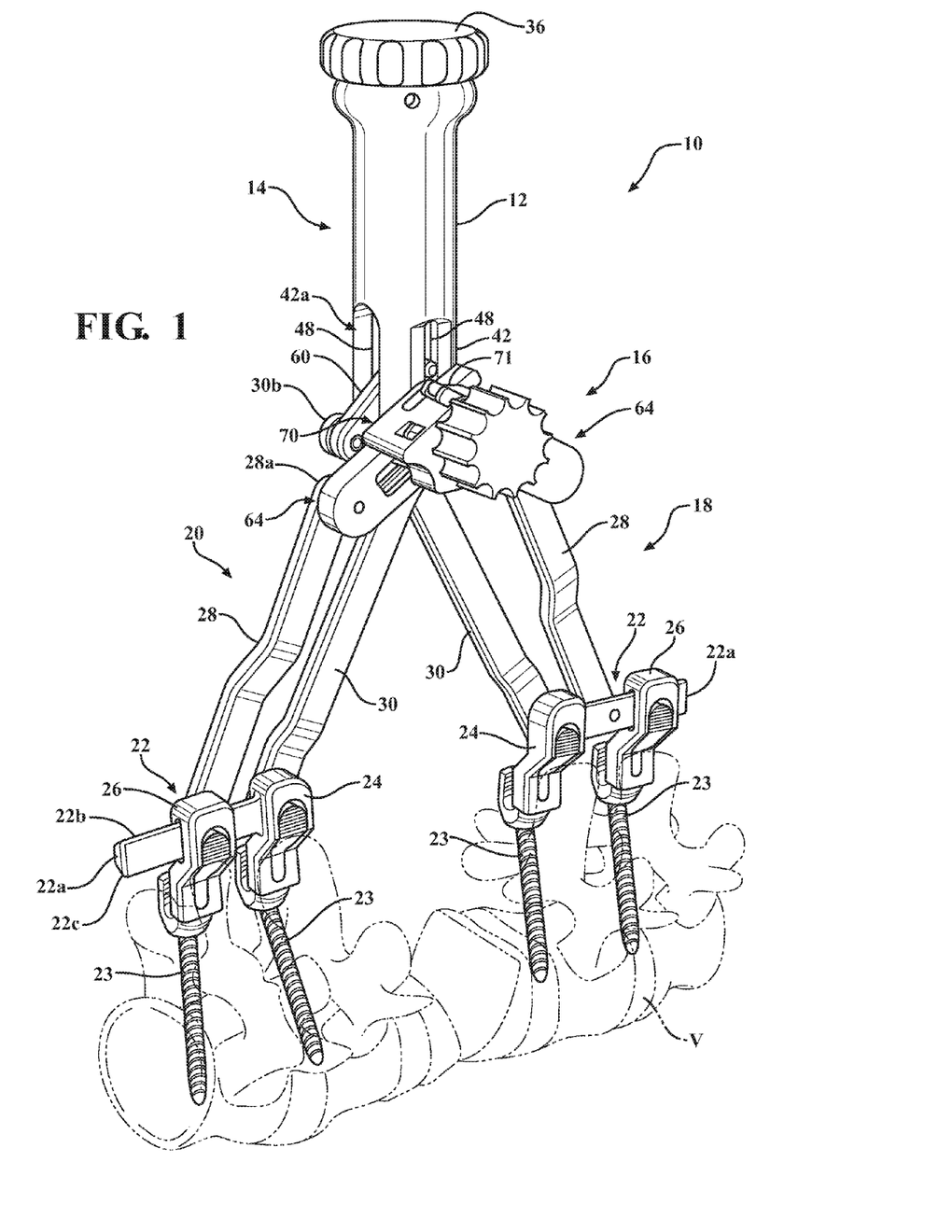
FIG. 1 is a front perspective view of an osteotomy instrument.
Figure 2:
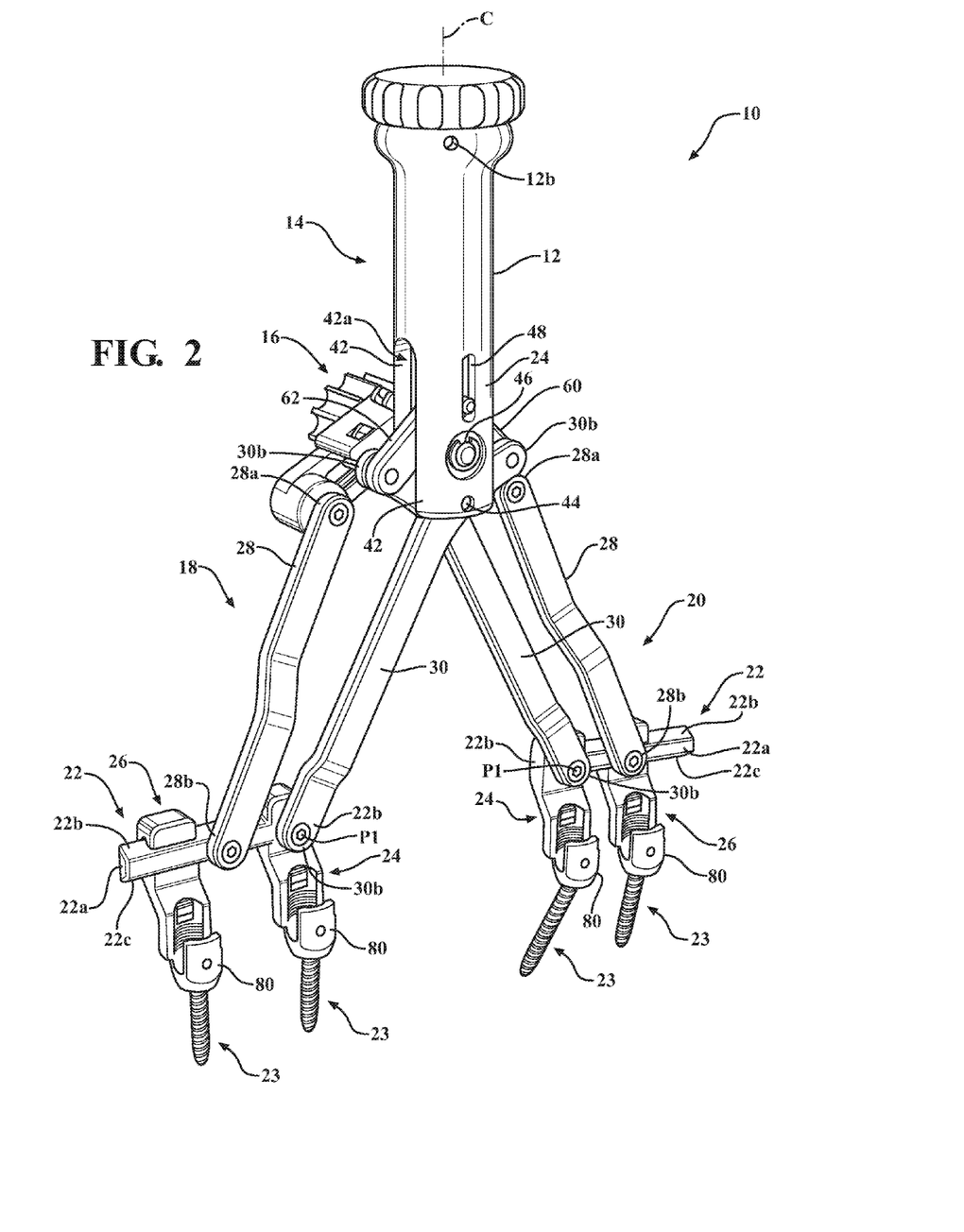
FIG. 2 is a rear perspective view of the osteotomy instrument.

With reference now to FIGS. 1 and 2, a front view of an illustrative embodiment of the osteotomy instrument 10 is provided. The instrument 10 may be formed of a polyetheretherketone, titanium, or any other material having sufficient structural rigidity to support implantation of an implant device and which is also approved for medical use. The osteotomy instrument 10 includes a handle 12, a displacing mechanism 14, a tuning mechanism 16, and a first arm assembly 18 and a second arm assembly 20 pivotably mounted to the handle 12. FIG. 1 shows the instrument 10 engaged with a vertebrae V so as to stabilize the vertebrae for a surgical procedure.

With reference again to FIGS. 1 and 2, the first and second arm assemblies 18 and 20 include a first and second fastener supports 22. The first and second fastener supports 22 are configured to hold a pair of fasteners 23. The fasteners 23 are optionally pedicle screws.

Figure 6:
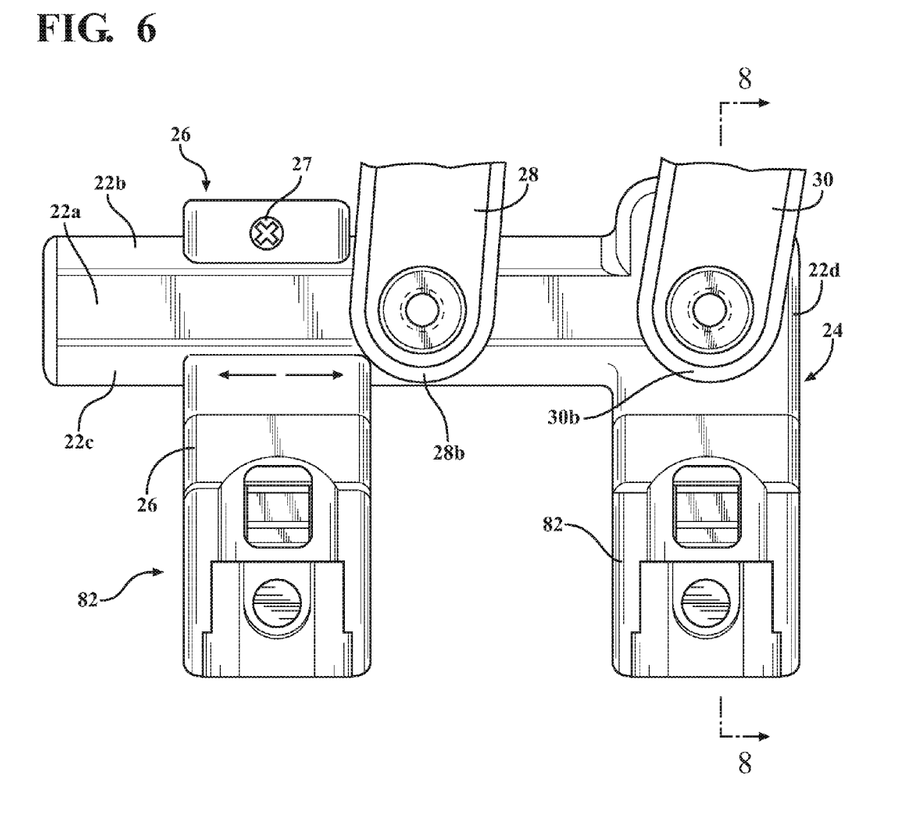
FIG. 6 an isolated view showing a pair of fastener housings mounted to the fastener support.

The fastener supports 22 include a generally elongated member 22a having a first angled surface 22b and a second angled surface 22c so as to form a generally trapezoidal cross section. A pair of fastener housings 24, 26, namely an inner fastener housing 24 and an outer fastener housing 26, are mounted to the first and second fastener supports 22. The inner fastener housing 24 may be integrally formed to a distal end 22d of the fastener supports 22 and the outer fastener housing 26 is slidably mounted to the trapezoidal cross section of the elongated member 22a, as shown in FIG. 6.

The first and second arm assemblies 18 and 20 each include an outer primary arm 28 having a proximal end 28a and an opposite distal end 28b. The proximal ends 28a of the outer primary arms 28 are fixedly secured to the first and second fastener housings 22, respectively. The distal ends 28b of the outer primary arms 28 are attached to the tuning mechanism 16, which will be described in greater detail below.

The first and second arm assemblies 18 and 20 each include an inner secondary arm 30 having a proximal end 30a and an opposite distal end 30b. The proximal ends 30a of the inner secondary arms 30 are pivotably attached to first and second fastener housings 22 adjacent the distal 22d of the fastener housings 22. Specifically, the distal ends 30a of the inner secondary arms 30 are pivotal about a pivot axis P1 with respect to the fastener housings 22.

With reference now to FIGS. 1-4, the displacing mechanism 14 is configured to laterally displace the distal ends of the first and second arm assemblies 18, 20 with respect to each other. Specifically, the displacement mechanism 14 laterally displaces the distal ends 22d of the first and second fastener supports 22 to increase and decrease the distance therebetween.

It is appreciated that the term "laterally" refers to a direction orthogonal to a longitudinal axis C of the handle 12. Namely, the displacing mechanism 14 is configured to laterally displace the distal ends 30b of the respective inner secondary arms 28 towards or away from each other.

Figure 3:
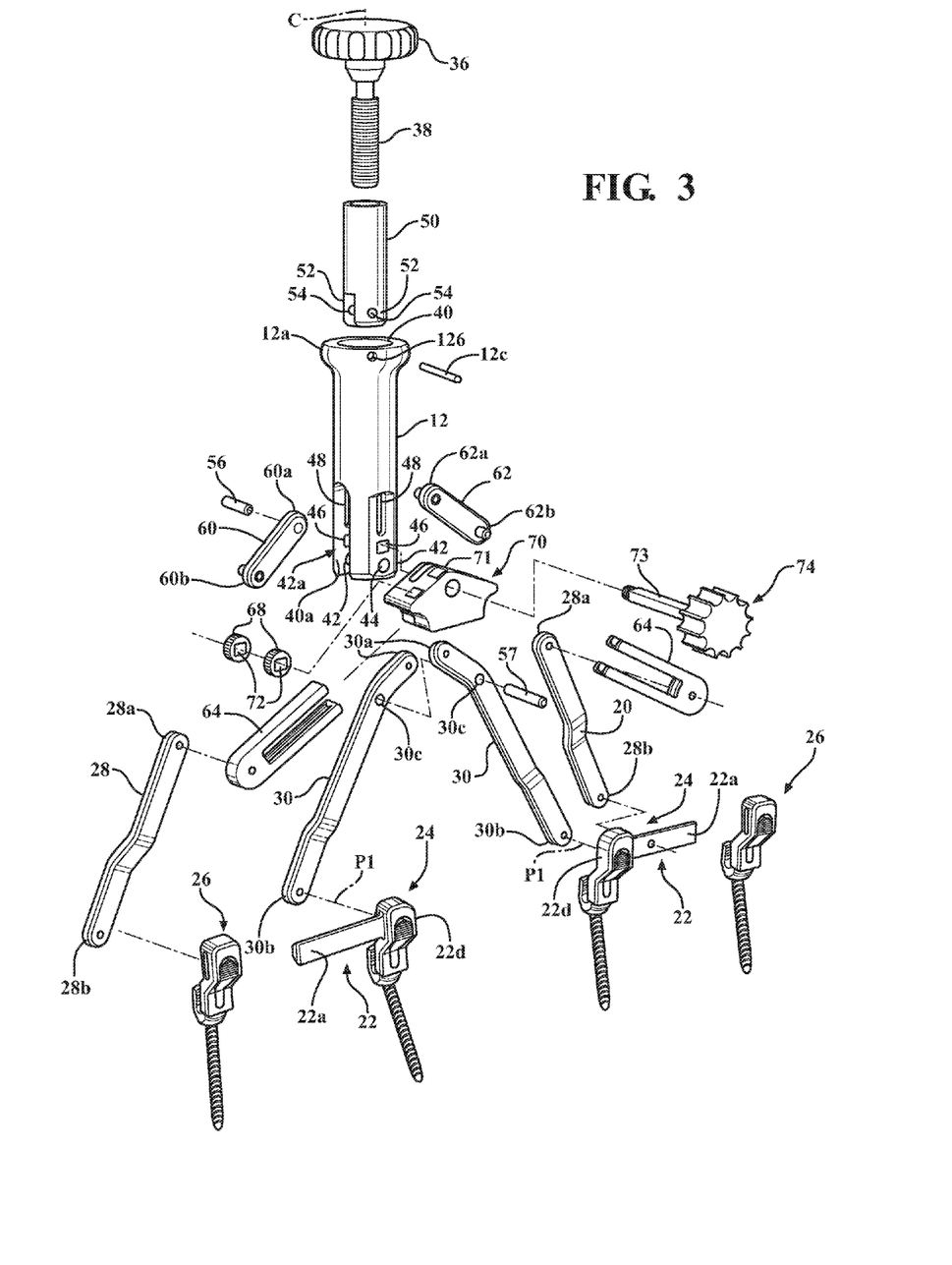
FIG. 3 is an exploded view of the instrument of FIG. 1.
Figure 4:
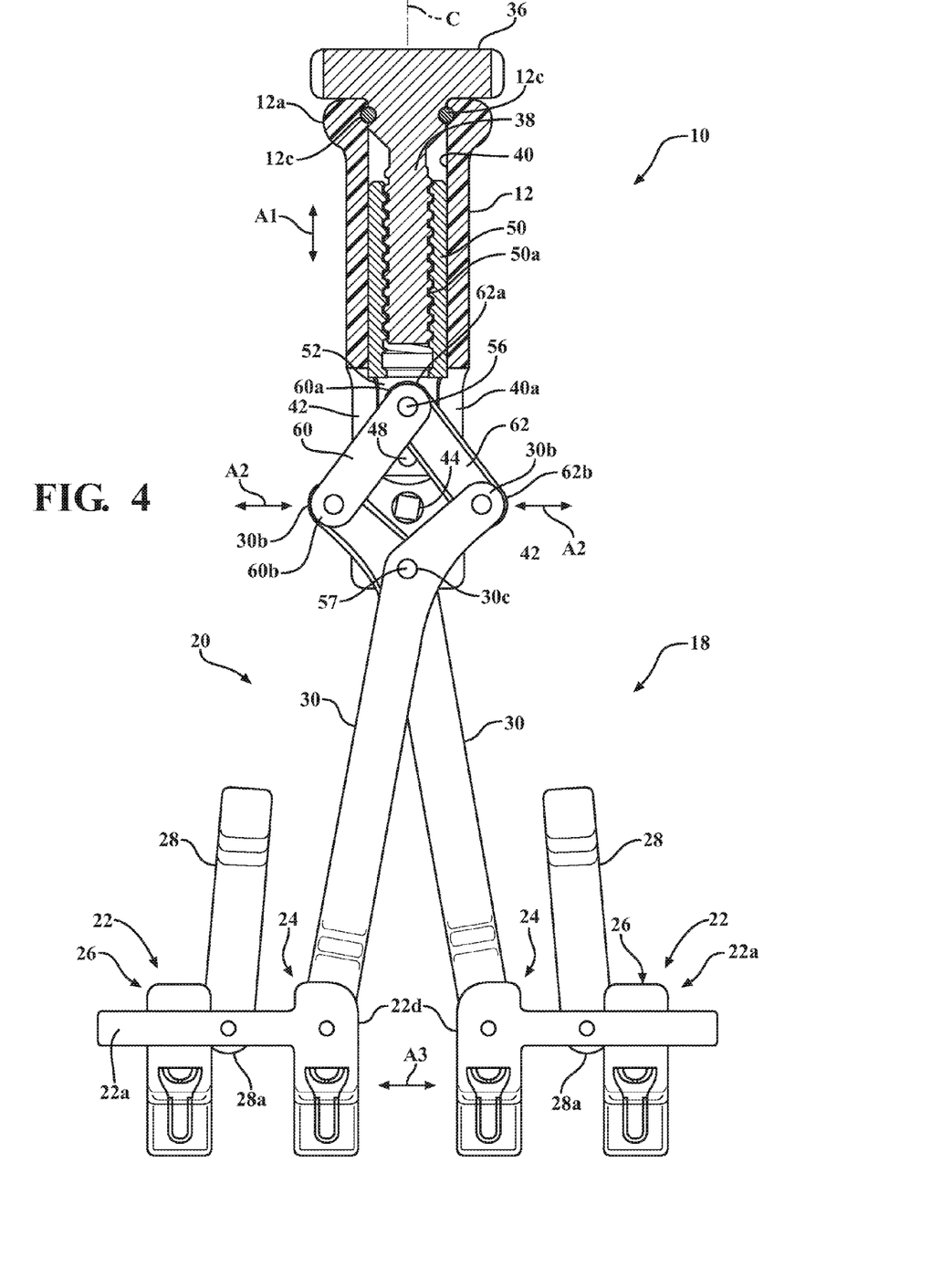
FIG. 4 is a partial cross-sectional view showing the operation of a displacement mechanism.

With reference now to FIGS. 3 and 4, a description of the preferred embodiment of a displacing mechanism 14 is provided. The displacing mechanism 14 includes a rotary member such as a dial 36 having a threaded shaft 38. The handle 12 includes bore 40 defining a top opening 12a. The handle 12 includes a retainer pin hole 12b that receives a retainer pin 12c. The retainer pin 12c is received within the retainer pin hole 12b and an annular collar 12d between the dial 36 and the threaded shaft 38. The engagement of the retainer pin 12c within the retainer pin hole 12b and the collar 12d prevents the dial 36 from moving linearly with respect to the longitudinal axis C of the handle.

The handle 12 includes a pair of arms 40a opposite the top opening 12a. The pair of arms 42 defines an opening 42a therebetween. The dial 36 is disposed within a top opening 12a of the handle 12. The handle 12 further includes a pair of pinholes 44 and a pair of rod holes 46 disposed on each of the pair of arms 42. An elongated slot 48 is disposed on each of the pair of arms 40a between the pair of rod holes 46 and the top opening 12a of the handle. The pair of rod holes 46 are positioned between the elongated slots 48 and the pair of pin holes 44.

The displacing mechanism further includes a hollow stud 50 dimensioned to slidingly fit within the bore 40 of the handle 12. The stud 50 is disposed within the bore 40 of the handle 12. The stud 50 is formed with internal threads 50a, best seen in FIG. 4, that correspond to the threaded shaft 38 of the dial 36. The stud 50 includes a pair of arms 52, and a pair of stud pin holes 54 disposed on each of the pair of arm 52. The pair of stud pin holes 54 are configured to receive a stud pin 56. The threaded shaft 38 of the dial 36 is configured to engage the internal threads 50a of the stud 50.

The displacing mechanism 14 includes a first leg 60 and a second leg 62. The first leg 60 includes a proximate end 60a and an opposite distal end 60b. The second leg 62 includes a proximate end 62a and an opposite distal end 62b.

As shown in FIGS. 3 and 4, the proximal end 60a of the first leg 60 and the proximate end 60a of the second leg 62 are mounted to the stud 50 via the stud pin 56 and pair of stud pinholes 54. The stud pin 56 pivotably couples the proximal ends 60a and 62a of the first and second legs 60 and 62, respectively, to the stud 50. The stud pin 56 extends beyond the pair of arms 52 of the stud 50 and extends within each of the elongated slots 48 form in each of the pair of arms 52. The stud pin 56 secures proximal ends 60a and 62a of the first and second legs 60 and 62, respectively, together so as to allow the first and second legs 60 and 62 to pivot about the stud pin 56, while the second slot 48 restricts the axial movement of the stud 50.

The distal end 60b of the first leg 60 is pivotably coupled to the proximal end 30a of the inner secondary arm 30 of the first arm assembly 18. The distal end 62b of the second leg 62 is pivotably coupled to the proximal end 30a of the inner secondary arm 30 of the second arm assembly 20.

Each of the inner secondary arms 30 of the first and second arm assemblies 18 and 20 include a pin hole 30c. The inner secondary arms 30 of the first and second arm assemblies 18 and 20 are pivotably attached to the each of the pair of arms 42 of the handle 12 by a pin 57 extending through the pair of pin holes 44.

In operation, rotation of the dial 36 moves the stud 50 up and down the threaded shaft 38 in the direction of arrow A1. As the first and second legs 60 and 62 are fixed to the stud 50, via the stud pin 56 and the pair of stud pin holes 54, and pivotably coupled to proximal ends 30a of the inner secondary arms 30, axial movement of the stud 50 stretches or compresses a distance between the distal ends 60a and 62b of the first and second legs 60 and 62, in the direction of arrow A2.

The compression or stretching of the distance between the distal ends 60a and 62b of the first and second legs 60 and 62 displaces the proximal ends 30a of the inner secondary arms 30 away from or towards each other and pivots the inner secondary arms 30 about the pin 57 thus displacing the distal ends 30b of the inner secondary arms 30 away from or towards each other to increase or decrease a distance between the distal ends 22d of the fastener supports 22 in the direction of arrows A3.

Figure 5:
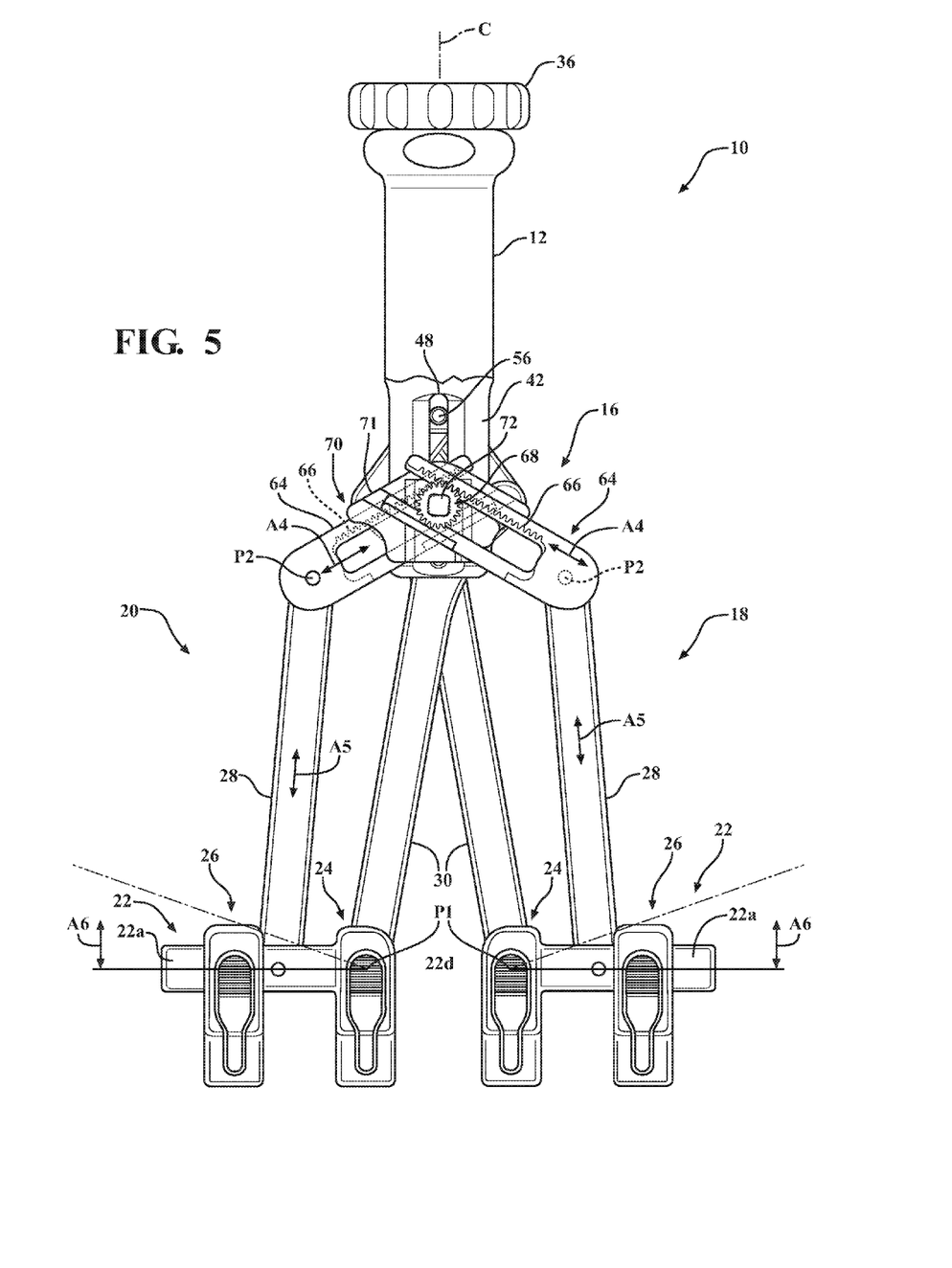
FIG. 5 a partial cross-sectional view showing the operation of a tuning mechanism.

With reference again to FIGS. 1-3 and now to FIG. 5 an illustrative view of the tuning mechanism 16 is provided. The tuning mechanism 16 may be disposed on an exterior side of the handle 12 adjacent one of the pair of arms 42. The tuning mechanism 16 is operable to displace the distal ends 28b towards and away from each other so as to pivot the fastener supports 22 about the pivot axis P1, and thus changes the angular position of the first fastener support 22 with respect to the second fastener support 22.

The tuning mechanism 16 is configured to act on the outer primary arms 28. The distal ends 28b of the outer primary arms 28 of the first and second arm assemblies 18 and 20 are fixedly mounted to the first and second fastener supports 22. As discussed above, the distal ends 30b of the inner primary arms 30 of the first and second arm assemblies 18 and 20 are pivotably mounted to the first and second fastener supports 22 about pivot axis P1.

The tuning mechanism includes a pair of U-shaped brackets 64. Each U-shaped bracket 64 includes a set of teeth 66 disposed within the inner surface of the U-shaped bracket 64 and configured to engage one of a pair of wheel gears 68. The U-shaped brackets 64 are generally laid on top of each other are received within a pair of slots 71 formed in a carrier 70. The carrier 70 is secured to one of the pair of arms 42 of the handle. The pair of U-shaped brackets 64 are slidably received within the pair of slots 71 such that the pair of U-shaped brackets 64 are slidingly displaceable with respect to the carrier 70.

The pair of wheel gears 68 are received within the interior of the U-shaped brackets 64. Each of the pair of wheel gears 68 include a hole 72. The hole 72 is shaped so as to fittingly seat on a rod 73 of a tuning dial 74. In particular, the rod 73 has a generally square cross-section so as to turn the pair of wheel gears 68. The pair of wheel gears 68 are shown as having a generally square-shaped hole 72. However, it should be appreciated that any other shape having a form fit engagement configured to rotate the pair of wheel gears 68 upon rotation of the tuning dial 74 may be used.

The rod 73 of the tuning dial 74 extends through a through hole formed in the carrier 70 and through the pair of rod holes 48 formed in the arms 42 of the handle. Each of the proximal ends 30a of the outer primary arms 28 of the first and second arm assemblies 18 and 20 are pivotably attached to the pair of U-shaped brackets 64 about pivot axis P2.

In operation, rotation of the tuning dial 74 engages the teeth of the pair of wheel gears 68 with the teeth 66 of the inner surface of the U-shaped brackets 64, which in turn slides the U-shaped brackets 64 within the slots 71 of the carrier 70 in the direction of arrow A4, based upon the rotation of the tuning dial 74.

As the proximal ends 28a of the outer primary arms 28 are pivotably mounted to the U-shaped bracket 64, the movement of the U-shaped brackets 64 provides a pushing or pulling action on the outer secondary arms 28, in the direction of arrow A5.

The movement of the outer secondary arms 28 causes the first and second fastener supports 22 to pivot about the pivot axis P1 to adjust the angular position of the first fastener housing 22 with respect to the second fastener housing 22, in the direction of arrows A6. The pivotably movement of the first and second fastener supports 22 also adjusts an angle formed between a longitudinal axis L of the first and second fastener supports 22 with the longitudinal axis C of the handle 12.

Figure 7:
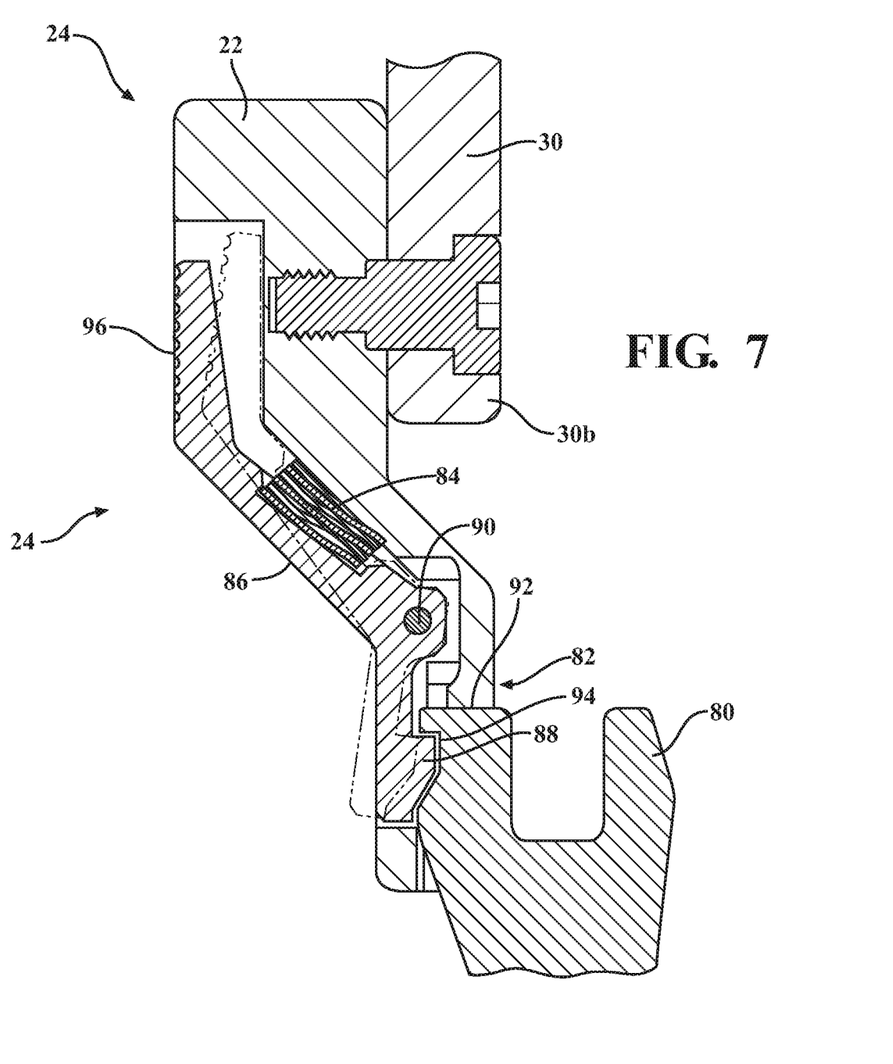
FIG. 7 is a partial cross-sectional taken along line 8-8 of FIG. 7 showing an eject mechanism.

With reference now to FIGS. 6 and 7, an illustrative view of the first and second fastener supports 22, the inner fastener housings 24, and the outer fastener housings 26 are provided. Each of the first arm assembly 18 and the second arm assembly 20 includes an inner fastener housing 24 and an outer fastener housing 26. The inner fastener housing 24 is integrally formed to the fastener support 22. The inner fastener housings 24 are provided adjacent to the pivot axis P1 in which the fastener support 22 is pivotably mounted to the distal ends 30b of the inner secondary arms 30.

The distal ends 28b of the outer primary arm 28 are fixed to the fastener supports 22 and spaced apart from the distal ends 30b of the inner secondary arms 30. The distal end 28b of the outer primary arm 28 is laterally displaced from the distal ends 30b of the inner secondary arms 30.

The outer fastener housing 26 is slidably attached to the fastener support 22. The fastener support 22 includes a first angled surface 22b and a second angled surface 22c so as to form a generally trapezoidal cross section. The outer fastener housing 26 includes a slotted support configured to engage the trapezoidal shaped pedicle screw support 22. A set screw 27 may be used to fix the outer fastener housing 26 to a predetermined position along the elongated member 22a of the fastener support 22.

A receiver 80 of the fastener 23 is releasably engaged to the inner and outer fastener housings 24, 26. An ejector mechanism 82 is disposed within the fastener housings 24, 26. The ejector mechanism 82 includes a biasing member 84, a lever 86, an engagement member 88, and a pin 90, and an undercut 92. The lever 86 is pivotal about the pin 90 between an engaged position and a disengaged position, shown in ghost in FIG. 7. The biasing member 84 is configured to bias the lever 86 into an engaged position.

In the engaged position the engagement member 88 is received within a notch 94 formed on the receiver 80. The engagement member 88 retains the receiver 80 in abutting contact with the undercut 92.

Actuation of a proximal end 96 of the lever 86 compresses the biasing member 84 and pivots the lever 86 about the pivot pin 90 releasing the engagement member 88 from the notch 96 formed in the receiver 80. Accordingly, the rod receivers 80 may be disengaged from respective inner and outer fastener housings 24, 26.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination.

It is claimed:

1. An osteotomy instrument comprising:
    a handle having a bore,
    a first arm assembly pivotably mounted to the handle about a first pivot pin, the first arm assembly having a first fastener support configured to hold a pair of fasteners;
    a second arm assembly pivotably mounted to the handle about the first pivot pin, the second arm assembly having a second fastener support configured to hold a pair of fasteners;
    a displacing mechanism having a dial disposed on the handle, the displacing mechanism further includes a stud having a threaded inner wall, the first pivot pin fixed to the stud, the stud slidingly engaged with the bore of the handle and configured to translate a rotation of the handle into the axial displacement of the stud in a direction coaxial to a longitudinal length of the handle, wherein the displacement of the stud laterally pivots the first and second arm assembly about the first pivot pin so as to displace a distal end of the first arm assembly and second arm assembly away and towards each other, the dial actuating the displacing mechanism; and
    a tuning mechanism configured to change an angular position of the first fastener support with respect to the second fastener support.

2. The osteotomy instrument as set forth in claim 1, wherein each of the first arm assembly and the second arm assembly includes an outer primary arm and an inner secondary arm, each of the outer primary arm and the inner secondary arm of the first arm assembly includes a distal end attached to the first fastener support, and each of the outer primary arm and the secondary primary arm of the second arm assembly includes a distal end attached to the second fastener support.

3. The osteotomy instrument as set forth in claim 2, wherein, the dial further includes a threaded shaft configured to engage the bore so as to move the stud up and down the handle, and wherein movement of the stud up and down the handle laterally displaces fastener supports attached to distal ends of the first arm assembly and the second arm assembly away and towards each other.

4. The osteotomy instrument as set forth in claim 3, wherein the displacing mechanism includes a first leg and a second leg, the first leg has a distal end pivotably attached to a proximal end of the inner secondary arm of the first arm assembly and the second leg has a distal end pivotably attached to a proximal end of the inner secondary arm of the second arm assembly, and
    wherein the inner secondary arm of the first arm assembly and the inner secondary arm of the second arm assembly are pivotably attached to the handle by an inner secondary pin at a position on the inner secondary arm of the first arm assembly between the proximate end and the distal end and on the inner secondary arm of the second arm assembly between the proximate end and the distal end.

5. The osteotomy instrument as set forth in claim 4, wherein the first leg has a proximate end opposite the distal end and the second leg has a proximate end opposite the distal end, the proximate end of the first leg and the proximate end of the second leg are pivotably attached to a stud pin, and the stud pin is attached to the stud, wherein the movement of the stud displaces the stud pin which linearly displaces the proximate end of the first leg and the proximate end of the second leg, the linear displacement of the proximate end of the first leg and the proximate end of the second leg pivots the inner secondary arm of the first arm assembly and the inner secondary arm of the second arm assembly about the inner secondary arm pin which laterally displaces the distal end of the first arm assembly and the distal end of the second arm assembly away and towards each other.

6. The osteotomy instrument as set forth in claim 2, wherein the tuning mechanism includes a pair of brackets having an interior surface with teeth, a tuning dial having a shaft, a pair of wheel gears attached to the shaft, each of the pair of wheel gears engaged with a respective one of the pair of brackets, the tuning dial rotatably mounted to the handle, and wherein the outer primary arm of the first arm assembly includes a proximate end pivotably attached to one of the pair of brackets, and the outer primary arm of the second arm assembly includes a proximate end pivotably attached to the other of the pair of brackets.

7. The osteotomy instrument as set forth in claim 6, wherein the tuning mechanism includes a carrier fixedly secured to the handle, the housing having a pair of guide slots, the pair of brackets slidably received within the pair of guide slots, the carrier defining a throughhole through which the shaft of the tuning dial extends, and wherein actuation of the tuning dial rotates the pair of gear wheels which displaces the pair of brackets within the pair of slots of the carrier to displace and pivot the proximate end of the outer primary arm of the first arm assembly and the proximate end of the outer primary arm of the second arm assembly to change the angular position of the first fastener support with respect to the second fastener support.

8. The osteotomy instrument as set forth in claim 7, wherein the distal end of the inner secondary arm of the first arm assembly is pivotably attached to the first fastener support and the distal end of the inner secondary arm of the second arm assembly is pivotably attached to the second fastener support, and wherein the outer primary arm of the first arm assembly is fixedly secured to the first fastener support and the outer primary arm of the second arm assembly is fixedly secured to the second fastener support.

9. The osteotomy instrument as set forth in claim 8, wherein each of the first fastener support and the second fastener support includes a receiver adapted to receive one of the pair of fasteners, each of the first fastener support and the second fastener support includes an ejector mechanism configured to retain and eject the receiver from the first and second fastener supports.

10. The osteotomy instrument as set forth in claim 9, wherein the ejector mechanism includes a biasing member and an engagement member formed on a lever pivotably attached to each of the first fastener support and the second fastener support, the lever is pivotal between an engaged position and a disengaged position, the biasing member biases the lever towards the engaged position, and wherein the engagement member is configured to retain the receiver within the first fastener support and the second fastener support when in the engaged position, wherein actuation of the lever disengages the engagement member from the receiver.

11. The osteotomy instrument as set forth in claim 10, wherein each of the first fastener support and the second fastener support includes a notch, and wherein in the engaged position the engagement member is received within the notch of the receiver to retain receiver against an undercut formed on the receiver.

12. An osteotomy instrument comprising:
a handle having a bore;
a first arm assembly pivotably mounted to the handle about a first pivot pin, the first arm assembly having a first fastener support configured to hold a fastener;
a second arm assembly pivotably mounted to the handle about the first pivot pin, the second arm assembly having a second fastener support configured to hold a fastener; and
a displacing mechanism having a dial disposed on the handle, the displacing mechanism further includes a stud having a threaded inner wall, the first pivot pin fixed to the stud, the stud slidingly engaged with the bore of the handle and configured to translate a rotation of the handle into the axial displacement of the stud in a direction coaxial to a longitudinal length of the handle, wherein the displacement of the stud laterally pivots the first and second arm assembly about the first pivot pin so as to displace a distal end of the first arm assembly and second arm assembly away and towards each other, the dial actuating the displacing mechanism.

13. The osteotomy instrument as set forth in claim 12, wherein each of the first arm assembly and the second arm assembly includes an outer primary arm and an inner secondary arm, each of the outer primary arm and the inner secondary arm of the first arm assembly includes a distal end attached to the first fastener support, and each of the outer primary arm and the secondary primary arm of the second arm assembly includes a distal end attached to the second fastener support, and wherein, the dial further includes a threaded shaft configured to engage the bore so as to move the stud up and down the handle, and wherein movement of the stud up and down the handle laterally displaces fastener supports attached to distal ends of the first arm assembly and the second arm assembly away and towards each other.

14. The osteotomy instrument as set forth in claim 13, wherein the displacing mechanism includes a first leg and a second leg, the first leg has a distal end pivotably attached to a proximal end of the inner secondary arm of the first arm assembly and the second leg has a distal end pivotably attached to a proximal end of the inner secondary arm of the second arm assembly, and wherein the inner secondary arm of the first arm assembly and the inner secondary arm of the second arm assembly are pivotably attached to the handle by an inner secondary pin at a position on the inner secondary arm of the first arm assembly between the proximate end and the distal end and on the inner secondary arm of the second arm assembly between the proximate end and the distal end.

15. The osteotomy instrument as set forth in claim 14, wherein the first leg has a proximate end opposite the distal end and the second leg has a proximate end opposite the distal end, the proximate end of the first leg and the proximate end of the second leg are pivotably attached to a stud pin, and the stud pin is attached to the stud, wherein actuating the dial rotates the threaded shaft which engages the bore to move the stud up and down the handle, the movement of the stud displaces the stud pin which linearly displaces the proximate end of the first leg and the proximate end of the second leg, the linear displacement of the proximate end of the first leg and the proximate end of the second leg pivots the inner secondary arm of the first arm assembly and the inner secondary arm of the second arm assembly about the inner secondary arm pin which laterally displaces the distal end of the first arm assembly and the distal end of the second arm assembly away and towards each other.

16. The osteotomy instrument as set forth in claim 12, wherein each of the first fastener support and the second fastener support includes a receiver adapted to receive one of the pair of fasteners, each of the first fastener support and the second fastener support includes an ejector mechanism configured to retain and eject the receiver from the first and second fastener support, wherein the ejector mechanism includes a biasing member and an engagement member formed on a lever pivotably attached to each of the first fastener and the second fastener supports, the lever is pivotal between an engaged position and a disengaged position, the biasing member biases the lever towards the engaged position, and wherein the engagement member is configured to retain the receiver within the first fastener support and the second fastener support when in the engaged position, wherein actuation of the lever disengages the engagement member from the receiver.

17. An osteotomy instrument comprising:
a handle having a bore;
a first arm assembly pivotably mounted to the handle, the first arm assembly having a first fastener support configured to hold a fastener;
a second arm assembly pivotably mounted to the handle, the second arm assembly having a second fastener support configured to hold a fastener, wherein each of the first arm assembly and the second arm assembly includes an outer primary arm and an inner secondary arm, each of the outer primary arm and the inner secondary arm of the first am assembly includes a distal end attached to the first fastener support, and each of the outer primary arm and the secondary primary arm of the secondary arm assembly includes a distal end attached to the second fastener support; and
a tuning mechanism configured to change an angular position of the first fastener support with respect to the second fastener support, wherein the tuning mechanism includes a pair of brackets having an interior surface with teeth, a tuning dial having a shaft, a pair of wheel gears attached to the shaft, each of the pair of wheel gears engaged with a respective one of the pair of brackets, the tuning dial rotatably mounted to the handle, and
wherein the outer primary arm of the first arm assembly includes a proximate end pivotably attached to the one of the pair of brackets, and the outer primary arm of the second arm assembly includes a proximate end pivotable attached to the other of the pair of brackets.

18. The osteotomy instrument as set forth in claim 17, wherein the tuning mechanism includes a carrier fixedly secured to the handle, the carrier having a pair of guide slots, the pair of brackets slidably received within the pair of guide slots, the carrier defining a throughhole through which the shaft of the tuning dial extends, and wherein actuation of the tuning dial rotates the pair of gear wheels which displaces the pair of brackets within the pair of slots of the housing to displace and pivot the proximate end of the outer primary arm of the first arm assembly and the proximate end of the outer primary arm of the second arm assembly to change the angular position of the first fastener support with respect to the second fastener support.

19. The osteotomy instrument as set forth in claim 17, wherein each of the first fastener support and the second fastener support includes a receiver adapted to receive one of the pair of fasteners, each of the first fastener support and the second fastener support includes an ejector mechanism configured to retain and eject the receiver from the first and second fastener supports;

wherein the ejector mechanism includes a biasing member and an engagement member formed on a lever pivotably attached to each of the first fastener support and the second fastener support, the lever is pivotal between an engaged position and a disengaged position, the biasing member biases the lever towards the engaged position, and wherein the engagement member is configured to retain the receiver within the first fastener support and the second fastener support when in the engaged position, wherein actuation of the lever disengages the engagement member from the receiver.

* * * * *